United States Patent [19]

Leonard

[11] Patent Number: 5,298,115
[45] Date of Patent: Mar. 29, 1994

[54] PRODUCING PROSTHESES

[76] Inventor: Ian Leonard, 62 Thorns Road, Bolton Lancashire BL1 6PD, Great Britain

[21] Appl. No.: 856,029
[22] PCT Filed: Oct. 23, 1990
[86] PCT No.: PCT/GB90/01622
§ 371 Date: Jul. 6, 1992
§ 102(e) Date: Jul. 6, 1992
[87] PCT Pub. No.: WO91/07139
PCT Pub. Date: May 30, 1991

[30] Foreign Application Priority Data
Nov. 9, 1989 [GB] United Kingdom ............ 8925380

[51] Int. Cl.$^5$ .............. B44C 1/22; B29C 37/00; C23F 1/00
[52] U.S. Cl. ............................. 156/645; 156/643; 156/644; 156/659.1; 156/668; 156/345; 204/129.65
[58] Field of Search ............ 204/129.35, 129.55, 204/129.65; 156/643, 644, 645, 659.1, 668, 345

[56] References Cited

U.S. PATENT DOCUMENTS

| | | | |
|---|---|---|---|
| 3,325,319 | 6/1967 | Frantzen | 156/644 |
| 3,420,142 | 1/1969 | Gale | 144/136 R |
| 3,508,108 | 4/1970 | Salisbury | 156/644 X |
| 4,466,858 | 8/1984 | Poler | 204/129.65 X |

FOREIGN PATENT DOCUMENTS

| | | |
|---|---|---|
| 0187065 | 7/1986 | European Pat. Off. |
| 190543 | 8/1986 | European Pat. Off. |
| 290138 | 11/1988 | European Pat. Off. |
| 2920223 | 11/1980 | Fed. Rep. of Germany |
| 3516862 | 11/1986 | Fed. Rep. of Germany |
| 3724479 | 2/1989 | Fed. Rep. of Germany |

OTHER PUBLICATIONS

Production Engineer, Jun. 1987, pp. 14–16, "High Production Chemical Milling".
Patent Abstracts of Japan, vol. 13, No. 121 (E-732)(3469), JP-A-63-289990, Nov. 28, 1988, Tasuku Fujii, et al., "Manufacture of Printed Wiring Board".

*Primary Examiner*—William Powell
*Attorney, Agent, or Firm*—Oblon, Spivak, McClelland, Maier & Neustadt

[57] ABSTRACT

A method and apparatus for the production of prostheses used in orthopaedic and trauma surgery for pinning broken bones wherein the method includes the steps of predetermining the shape of the article required, selecting a sheet material blank from which the article is formed, processing the blank by removing material therefrom to leave an article of the predetermined shape or a processed blank from which an article of the predetermined shape is made by bending the blank, and removing the material using an etching process. The apparatus includes a blank processing device for predetermining the shape of the article required and processing the blank by removing material therefrom to leave an article of the predetermined shape or a process blank from which the article of the predetermined shape may be made by bending the blank. An etching device is provided for removing material from the blank.

15 Claims, 6 Drawing Sheets

PRODUCING PROSTHESES

TECHNICAL FIELD

This invention relates to the production of prostheses such as are used in orthopaedic and trauma surgery for pinning broken bones.

BACKGROUND ART

Conventionally, such prostheses are selected by the surgeon from a set or kit of standard sizes and shapes of plates or strips having pre-drilled holes for screws. These may be capable of some limited bending and/or cropping to adapt a specific size of strip or shape to more closely suit the circumferences of any particular fracture. Generally speaking, however, the type of pinning possible using these conventional prostheses is limited in scope because of their 2-dimensional configuration which is often unsatisfactory from both a surgical and mechanical strength point of view.

The difficulties involved in bending have led to proposals for mechanical aids to bending so-called osteosynthetic plates during surgery, such proposals being contained in DE-OS-37 24 479 and DE-OS-29 20 223. However, these aids do not facilitate anything like the full range of prosthetic shapes necessary and even so require still a considerable inventory of shapes and sizes of osteosynthetic plates.

A wider range of prosthetic shapes would facilitate different and better pinning techniques, but the prefabrication of a complete range would be a near-impossible task and the maintenance of a comprehensive inventory to cover all eventualities prohibitively expensive, to say nothing of the difficulty of selecting a shape and size from such a plethora of possibilities.

The custom-production of prostheses precisely adapted to a particular fracture has to date been substantially ruled out because of the time required to produce such prostheses by conventional production techniques and the lack, in any event, of workshop facilities close to the operating theater.

SUMMARY OF THE INVENTION

The present invention provides methods and apparatus for the production of articles that inter alia facilitate the rapid, on-site production of medically supervised custom-made prostheses.

The invention comprises a method for the rapid, one-off or small batch production of a shaped article such as a surgical prosthesis characterized by comprising the steps of
a) predetermining the 3-dimensional shape of the article required,
b) selecting a sheet material blank from which the article may be formed,
c) processing the blank by removing material therefrom to leave an article of the predetermined shape or a processed blank from which an article of the predetermined shape may be made by bending the blank, and
d) the material being removed using an etching (which may be an electrochemical machining) process in which resist is removed by a computer aided design/manufacturing method.

Usually, the material will be 18/8 type stainless steel, but the development of other medically suitable materials such as titanium or plastics cannot be ruled out.

The blank may be prepared with fold lines which may be made by etching or, more rapidly, by electrochemical machining (ECM). Features other than fold lines may also be etched such for example as apertures as for screws and pins and the required perimeter of the prosthesis.

Although removing the resist layer could be done by the usual photographic methods, these are seen as unacceptably slow, as currently practiced. So the acid resist layer, which may comprise a wax, collodial gel or plastic or rubber adhesive film coating, may be removed mechanically as by a blade, a rotary tool or an ultrasonic tool, or by vaporization as by an electric discharge or laser. The resist layer may also be removed by selectively applying a chemical reagent or solvent as by an airbrush or jet printer. The resist may also, of course, be selectively applied, rather than applied overall and then removed selectively.

The blank may be etched concurrently on both faces, especially for the production of screw and/or pin apertures and the perimeter, but also for producing oppositely-directed curved regions. Etching of such features can leave sharp ridges or burrs, which can be removed by electropolishing. Screw and/or pin apertures or holes may also be produced by a drill or punch or other purely mechanical means where convenient.

The blank may be processed using numerically-controlled tool means, such as a blade or rotary tool, laser or an airbrush or jet printer applying a reagent or solvent, and may be prepared, for example on an X-Y table or CAD type plotter, according to instructions derived from a programmed computer supplied with data specifying the shape of the prosthesis required. The computer may control the blank preparation and the CAD facility may involve the use of X-ray photographs of the prosthesis site.

Various improvements may be made on conventional ECM techniques which usually require a pre-shaped three dimensional tool to remove metal from a surface. Thus applying a resist layer to the workpiece as for normal etching techniques ensures that only the exposed metal areas are removed. Instead of applying the resist to the workpiece, however, the resist may be on the tool, and removed therefrom according to the desired pattern. The workpiece will be eroded more or less as if it had carried the resist, but there is no longer any need to remove the resist from the workpiece after the ECM operation, which cuts down the manufacturing time significantly.

Another technique involves interposing an apertured non-conducting layer e.g. of plastic sheet between the electrode and the workpiece. The apertures may be made by a rotating tool, a laser, and ultrasonic cutter or in any other convenient manner. Here, again, there is no adhered resist layer to remove after the ECM.

The invention also comprises apparatus for the production of prostheses from preformed blanks comprising blank processing means predetermining the shape of prosthesis required and processing the blank by removing material therefrom to leave a prosthesis of the predetermined shape or a processed blank from which a prosthesis of the predetermined shape may be made by bending the blank, charactized by etching (which may be electrochemical machining) means to remove material from the blank using a resist, and computer aided resist removal means.

BRIEF DESCRIPTION OF THE DRAWINGS

Embodiments of apparatus and methods for the production of prostheses according to the invention will now be described with reference to the accompanying drawings, in which.

BEST MODE FOR CARRYING OUT THE INVENTION

FIGS. 1 to 13 illustrate the production of prostheses 11 such as are used in surgery for pinning broken bones. The prostheses may take various general shapes, sizes and thicknesses according to the purpose for which they are being implanted.

Besides the commonly encountered fractures of the main bones of the arms and legs where the currently available predrilled strip prostheses are generally quite satisfactory, there are many other types of bone fracture repairs that would benefit from customized 3-dimensional curved plate protheses:

(1) Spinal—where the many small vital vertebrae need fine and particular support (2) Pelvic—a common injury in motor accidents, where the complex shape of the bone and the radiating nature of the fracture paths need large plates rather than several strips to be really effective (3) Periarticulate—that is to say close to the main joints where several or all of the adjacent bones are broken close to their sockets, a common sporting injury for which repair often needs special plates because of the confined access (4) Pathological—where large parts of bones have to be surgically removed because of tumors, cancer or incorrect bone growth, requiring the bones to be bridged until new bone growth knits the separated ends together (5) Internal and temporary fixation—where individual specially tailored long plates are needed for instance for rejoining and pinning of the sternum after open heart surgery.

(6) Facial—where jaw, cheek or brow bone is broken and depressed—a common result in motor accidents with impact on to the steering wheel or facia. Thin curved platelets to restore the original facial contours would aid cosmetic surgery.

(7) Multiple fractures—caused by bomb blast or bullets—need enveloping plates to support the various bone fragments, allowing them to knit correctly and ensuring true limb orientation.

In these seven examples of major surgical areas it is often difficult or impossible to predetermine the required implant configuration until very shortly before the prosthesis is needed—it is often not until surgery is actually in progress that the required shape can be decided upon. What the surgeon really requires is a custom-made plate produced in a very short time within the hospital itself to a shape and size specified shortly before or actually during the operation.

The production of shaped articles from stainless steel plates by etching fold lines and other features is already known, but as currently practiced does not lend itself to rapid custom production. The resists in common use are photographic and the etching pattern is produced by photographing a master drawing, usually involving a reduction of scale so that high accuracy can be achieved. It is not economical to use this process to produce articles on a one-off basis and it would in any event be difficult to complete a 15×5 cm from concept to finished state in less than five hours, even if the production were to be given priority and undivided attention. Normally, two or three days at least are required if the procedure is to fit within any ordered, commercial production schedule.

Photographic techniques may of course be developed in the future which will reduce the time and cost. Meanwhile, however, etched or electrochemically machined (ECM) plates can be produced by other methods which do not suffer the disadvantages of the current photographic techniques.

Figures 1, 4:
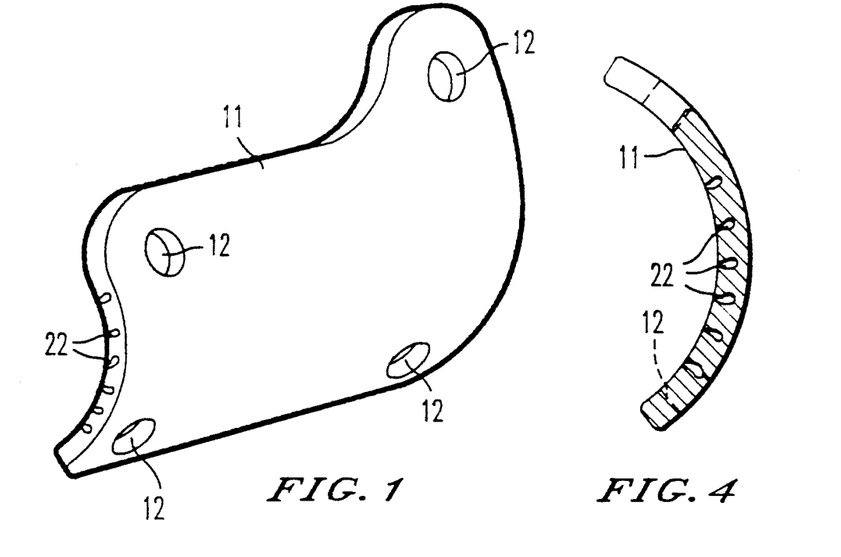
FIG. 1 is a perspective view of a typical curved 3-dimensional shaped prosthesis.
FIG. 4 is a sectional view like FIG. 3 after deformation to the required shape.

FIG. 1 illustrates a typical plate 11 which can readily be produced as herein described. It is designed to fit partically around sections of broken bone and be secured thereto by screws or pins for which matching holes 12 are provided.

The conventional techniques for joining bones have involved connecting the bones by flat plates using angled screws which, on tightening up, draw the broken ends into tight engagement. It is now thought to be better in fact to leave the ends separated by a small gap, for example a millimeter or less, which will eventually be bridged by new bone growth. This is well-nigh impossible using the conventional flat plate or strip, but is easily achieved using a 3-dimensional prosthesis as illustrated which has a degree of mechanical strength to support the bone structure.

Figure 2:
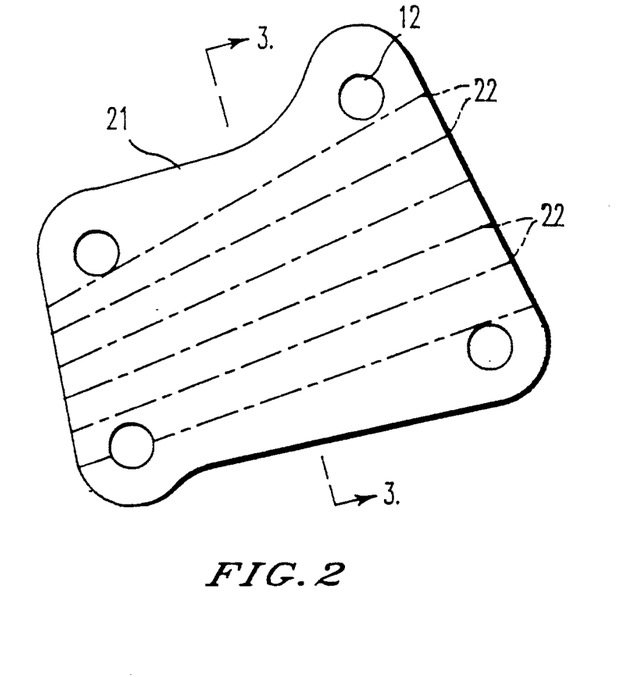
FIG. 2 is a developed plan view of a sheet material plate prepared for plastic deformation to the prosthesis of FIG. 1.
Figure 3:
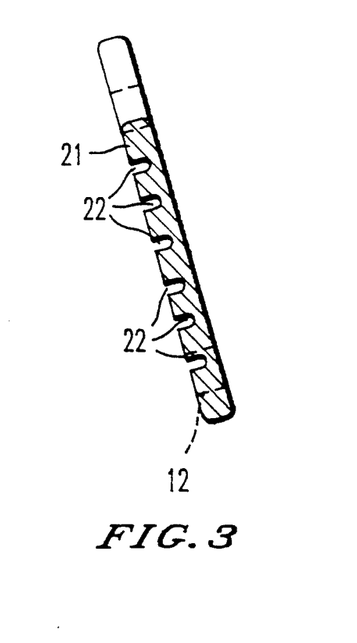
FIG. 3 is a sectional view taken along line III—FIG. 2 showing etched grooves and perpendicular hole areas.

The prosthesis 11 of FIG. 1 is made by plastic deformation of a blank 21 comprising a flat plate as shown in FIGS. 2 and 3 which has been etched or electrochemically machined with fold lines 22. Using suitably-positioned such fold lines, quite complicated shapes can be produced by deforming stainless steel plates—this can be done by hand or with the aid of a simple bending jig—the fold lines determining the extent to which the metal can be bent, and thus determining the final shape of the article with a high degree of precision.

FIG. 4 shows in cross-section the blank 21 after bending on the fold lines. As will be seen from the cross-section of FIG. 3, the fold lines are U-shaped grooves with angled sides and essentially the plate will fold easily along the line of the grooves until their corners come together and no further. The obtuse angle of the bend is determined by the width of the groove which is accurately prepared prior to etching or ECM. For example, a groove width equal to the material thickness will result in a near 90° included angle bend. It is therefore practical to provide a multi-faced polygon which approximates closely to a circular or elliptical curve by the number and width of parallel or diverging grooves. It will, of course, be possible for the surgeon to make small adjustments to the final shape, depending on the precise configuration of the fold lines and the material of which the plate is made.

Figure 5A:
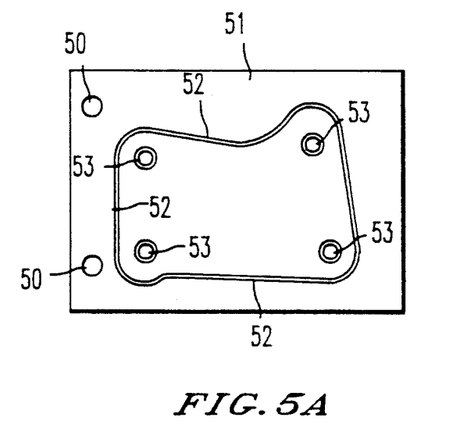
FIG. 5A is one face of a blank marked from predrilled datum centers comprising a sheet metal plate prepared for etching to make the developed plate of FIGS. 2 and 3.
Figure 5B:
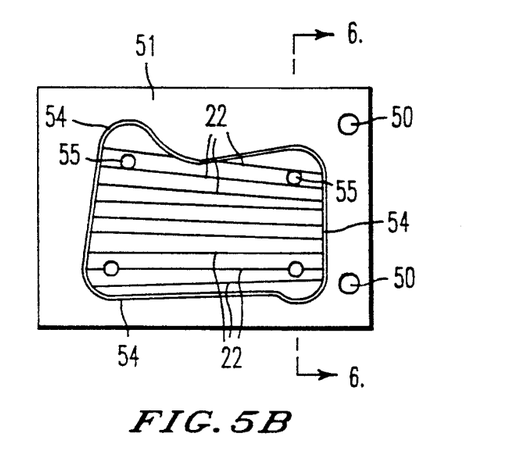
FIG. 5B is the reverse face of the sheet metal plate of FIG. 5A marked from the same datum centres.

FIGS. 5A and 5B show a sheet material plate 51 marked out on front (5A) and reverse (5B) faces for the production of the blank 21 of FIGS. 2 and 3. The plate 51 can, in a surgical situation, be selected from a range of sizes supplied as a set or kit for the purpose, once the overall dimensions of the prosthesis have been determined.

The face (5A) is marked with perimeter lines 52 and screwhole areas or outlines 53 relative to datum holes 50 predrilled in the prepared sheet, while the reverse is also marked with perimeter lines 54 precisely underneath the perimeter lines 52 and a mirror image using the identical datum holes 50. Screwhole areas or outlines 55 are marked on the reverse to a smaller diameter than the areas or outlines 53 to provide a countersink feature. For angled screws, the areas or outlines 55 can be offset as compared to the areas or outlines 53. The reverse is also marked with the fold lines 22. If curvature were required in opposite directions, so that parts of one face were convex while other parts were concave, fold lines would, of course, be produced on both faces.

By "marking" is meant, of course, the removal or modification of a resist, which may be a wax coating or a rubber or plastic film adhered to the metal surface to allow the etchant or ECM electrolyte access to the metal at the marked places.

Figure 6:
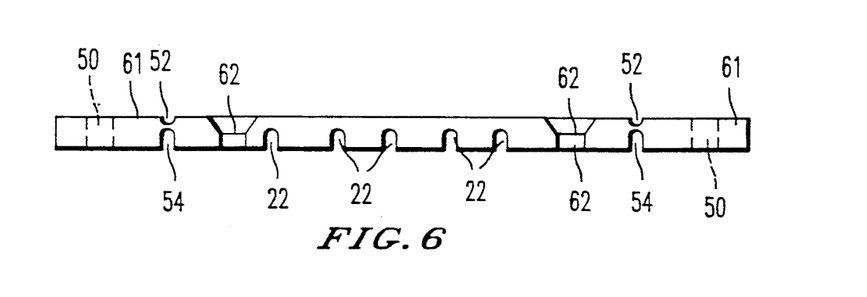
FIG. 6 is a sectional view taken along line VI—VI of FIG. 5A, after etching or ECM.
Figure 7:
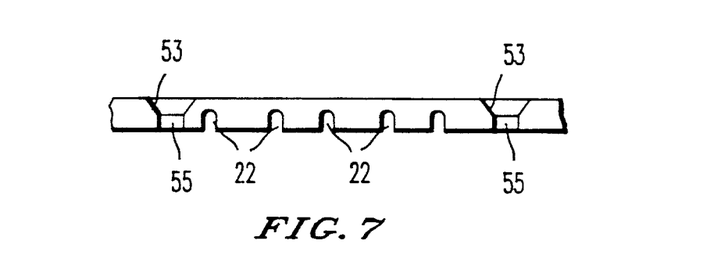
FIG. 7 is the sectional view of FIG. 6, after electropolishing.

After etching or ECM, the blank 21 looks, in cross-section, as shown in FIG. 6, where the trims 61 are shown, however, as still in position. In practice, these will fall or be broken off. The etching or ECM process leaves sharp burrs 62 here, however, which need to be removed. This is conveniently achieved by electropolishing, in which an electric potential is applied to the blank while in an etchant which effects rapid erosion of sharp features by comparison with flat regions, to leave the blank looking, in cross-section, as shown in FIG. 7.

Holes may be drilled or punched into the blank if the etching or ECM process is not double-sided, so as to speed up the process.

FIGS. 8 to 13 illustrate diagrammatically the sequence of operations involved in one method of producing the prosthesis 11 of FIG. 1.

Figure 8:
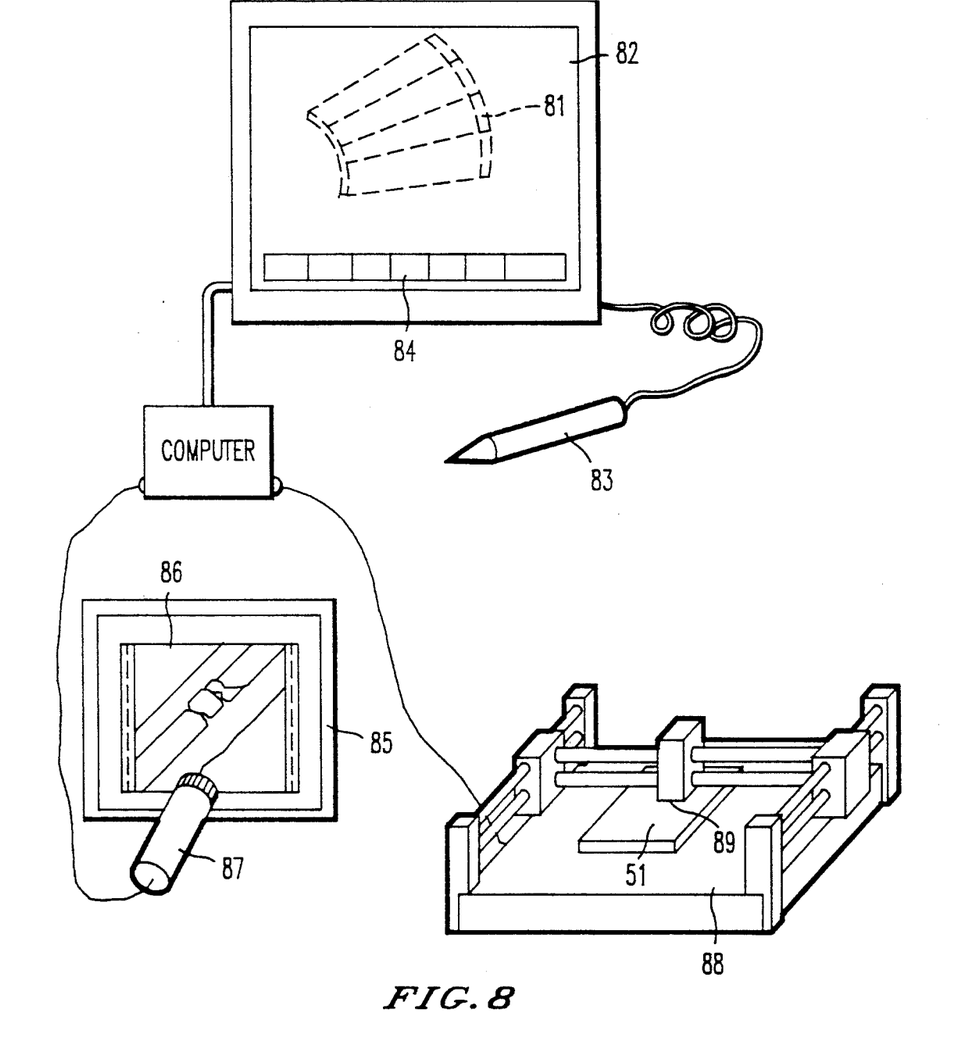
FIG. 8 is a diagrammatic illustration of a CAD/CAM system for producing a prepared blank ready for etching or ECM.

FIG. 8 illustrates a CAD/CAM arrangement in which the required prosthesis is modelled on an image 81 on a screen 82 using suitable CAD techniques which might for example involve a light, magnetic or inductive pen 83 to select features from a screen-displayed menu 84, and draw and dimension the skeletonized image 81. Available image-processing software can perform operations on the image 81 such as rotation, translation, stretching, reversing, scaling and so on. A light-box 85 is provided to illuminate an X-ray photograph 86 which can be viewed with a CCD camera 87 to produce an image on the screen 82 around which the prosthesis can be sketched using the light, magnetic or inductive pen 83. Software can, however, also be provided to analyse X-ray images taken from different angles to provide information from which a three-dimensional representation of the fracture site can be computed and from which, in turn, the required prosthesis shape can also be worked out according to algorithms, which might be compiled initially using an expert system, for example.

Software can also be provided then to calculate the size of blank required and to specify the fold lines and other features required to be marked to prepare the blank for etching or ECM so that it will deform into the required shape.

The computer can then control the operation of an X-Y plotter 88 equipped with a tool 89 for marking the plate 51 to produce the blank 21.

The tool 89 can be a blade or a rotary tool, for example a miniature air driven router, or a laser or electric discharge device to melt or vaporize a resist, or a pen or jet printer or air brush applying a reagent or solvent.

Figure 9:
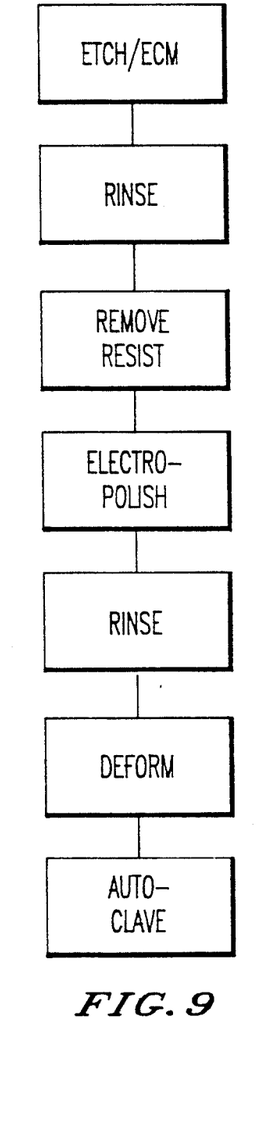
FIG. 9 is a diagrammatic representation of the production, by etching or by ECM using the method illustrated in FIG. 10, of a prosthesis, ready for implantation, from the prepared blank.

The marked blank is then subject to the sequence of operations indicated in FIG. 9, namely it is first of all etched or electrochemically machined, the rinsed, then the remaining resist is removed, following which it is re-etched or electro polished to remove sharp burrs left by the etching process, after which it is again rinsed. The thus prepared blank is now plastically deformed, by hand or bending tool on the fold lines, to its final shape as dictated by the fold lines, following which it is autoclaved to sterilize it ready for use.

Figure 10:
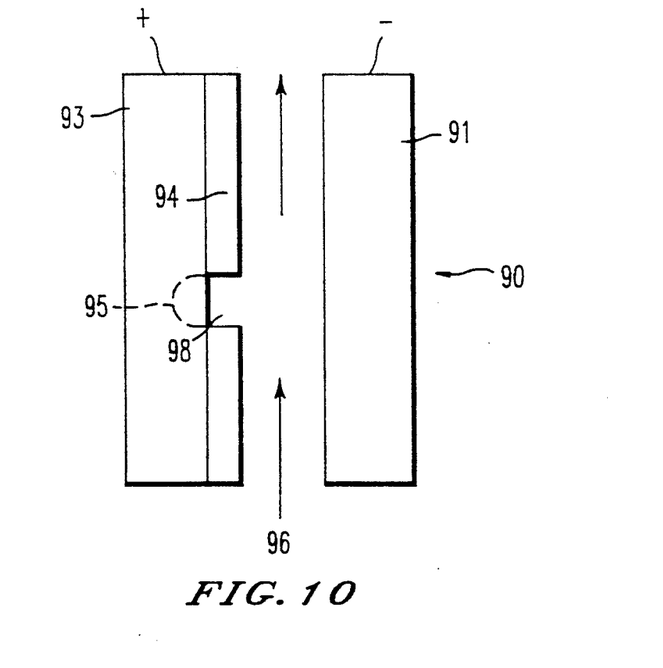
FIGS. 10, 11 and 12 are diagrammatic illustrations of electro-chemical machining techniques.

FIG. 10 shows diagrammatically a method of electrochemical machining (ECM). A flat metal electrode 91 (cathode) is aligned opposite the metal blank 93 (anode) which has the resist coating 94 with sections removed as at 95.

The said metal blank 93 and metal electrode 91 are connected to a source of direct current. Arcing is prevented by circulating an electrolyte 96, for example an hydroxide or ionized salt, or a conductive acid such as nitric or sulphuric, between the electrodes. Metal ions are taken into the electrolyte from the blank where the resist layer has been removed creating an etching 98 of the required dimensions.

Thereafter the metal blank 93 is rinsed and the remaining resist coating 94 is removed before electropolishing and the other steps shown in FIG. 9 to achieve a complete prosthesis.

Figure 11:
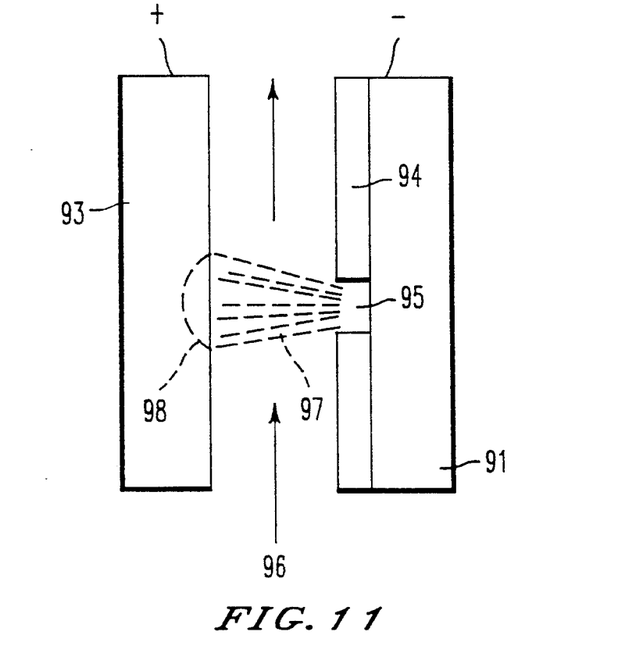
Figure 12:
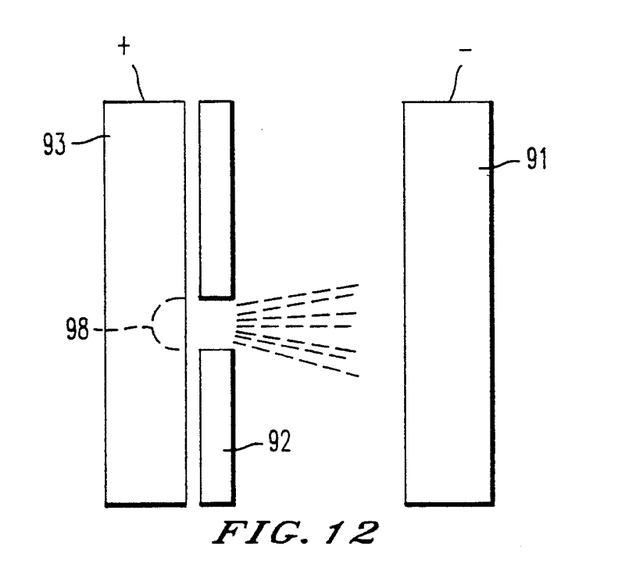

A different approach is shown in FIGS. 11 and 12. In FIG. 11 the metal blank 93 (anode) has no resist coating whatsoever. In fact the resist coating 94 with marked etching pattern 95 is located on the solid metal electrode 91 (cathode). As described with reference to FIG. 10, a current passes between the two electrodes as an electrolytic solution 96 flows therebetween to create an etching 98 in the metal blank 93.

FIG. 12 shows a further different approach, in which a non-conducting plastic sheet 92 is interposed between the blank 93 and the electrode 91, close to the blank. The sheet 92 is apertured as would be a resist by routing, laser or otherwise.

It may not always be necessary to circulate the electrolyte using this technique.

Figure 13:
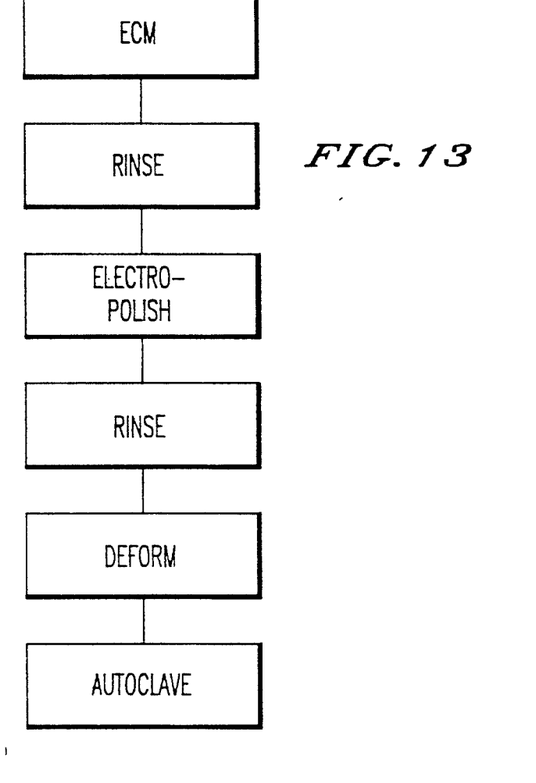
FIG. 13 is a diagrammatic representation of the production of a prosthesis, ready for implantation, from the prepared blank using the electro-chemical machining techniques of FIGS. 11 and 12.

An advantage of the improved methods described with reference to FIGS. 11 and 12, which is made clear in FIG. 13, is further time saving, since the metal blank is not coated in resist, therefore the time-consuming step of resist removal after etching is avoided.

While it has been suggested in the literature—see DE-OS 2 920 223—that point or spot loadings of an osteosynthetic plate against a bone should be avoided in favor of contact along the maximum possible surface area, it is now thought that when surrounding or partially surrounding a bone with a prosthesis as is proposed herein it is desirable not to contact the bone over large surface areas, rather by line contact as will follow from the polygonal cross-section of the prostheses naturally produced by the methods herein described so as not to completely occlude the bone.

Although numerous alternative procedures have been described within the context of the invention it is clear that yet further variations and modifications could be adopted which would remain within the overall concept.

The starting blank, if it does not require bending, may be nevertheless processed by metal removal techniques as discussed above, and plate stock need not then be used. For example, profiled rods or tubes may be designed and produced on-site by a CAD/CAM system from cylindrical or tubular metal stock, material being removed therefrom by ECM techniques for example to produce a final osteosynthetic prosthesis.

If other materials are used, plastics materials for example, they may be selectively modified as by UV illumination, low power laser, an ultrasonic horn or isotope radiation so as to cause shrinkage along lines on one face or the other that would bring about the required deformation.

And although the invention has been described with particular reference to surgical prostheses, it is clearly capable of producing shaped articles for other purposes where rapid, one or small batch production is called for, for example, in prototype development. The etching and ECM processes are especially useful in handling sheet materials which are not amenable to conventional machining or press work, for example, metals which workharden rapidly, full hardened metals used in thin springs, the glossy-amorphous alloys produced by super quenching, and the NiTi range of memory metals.

I claim:

1. A method for production of a shaped article, comprising the steps of:
   predetermining the shape of the article required,
   selecting a sheet material blank from which the article is formed,
   processing the blank by removing material therefrom to leave an article of the predetermined shape or a processed blank from which an article of the predetermined shape is made by bending the blank,
   the material being removed using an etching process in which a resist is removed by computer aided design.

2. A method according to claim 1, which comprises plastically deforming the processed blank to the required shape.

3. A method according to claims 1 or 2, which comprises preparing the blank with fold lines.

4. A method according to claim 1, which comprises preparing the blank with apertures.

5. A method according to claim 1, wherein the article is used for making a prosthesis, and wherein X-ray photographs of the prosthesis site are used in a computer aided design facility.

6. Apparatus for the production of shaped articles from preformed blanks, comprising:
   blank processing means for predetermining the shape of article required and processing the blank by removing material therefrom to leave an article of the predetermined shape or a processed blank from which an article of the predetermined shape may be made by bending the blank,
   etching means for removing material from the blank using a resist, and
   computer aided resist removal means.

7. Apparatus according to claim 6, wherein the etching means includes means for removing material so as to leave fold lines on the blank.

8. Apparatus according to claim 6, wherein the etching means comprises a cathode and a batch containing an electrolyte.

9. Apparatus according to any one of claims 6 to 8, wherein the blank is resist coated and marked for material removal.

10. Apparatus according to any one of claims 6 to 8, wherein the cathode is resist coated and marked for removal of metal from the blank.

11. Apparatus according to any one of claims 6 to 8, wherein an apertured non-conducting layer is interposed between an anode and cathode.

12. Apparatus according to any one of claims 6 to 8, wherein the electrolyte comprises one of an hydroxide, an ionizing salt solution and an acid.

13. Apparatus according to any one of claims 6 to 8, which comprises a resist coating removal means for removing the resist from the blank after etching by the etching means has occurred.

14. Apparatus according to any one of claims 6 to 8, which comprises electropolishing means for removing sharp edges and polishing the processed blank.

15. Apparatus according to any one of claims 6 to 8, which comprises numerically controlled tool means for marking one of the resist and a non-conducting layer on the blank.

* * * * *